(12) United States Patent
Krichevsky (10) Patent No.: US 9,944,907 B2
(45) Date of Patent: Apr. 17, 2018

(54) MUTATED LUX OPERON SEQUENCES (71) Applicant: BioGlow, L.L.C., St. Louis, MO (US)

(72) Inventor: Alexander Krichevsky, St. Louis, MO (US)

(73) Assignee: BioGlow LLC, St. Louis, MO (US)

( * ) Notice: Subject to any disclaimer, the term of this patent is extended or adjusted under 35 U.S.C. 154(b) by 0 days.

(21) Appl. No.: 14/687,601

(22) Filed: Apr. 15, 2015

(65) Prior Publication Data
US 2017/0044505 A1 Feb. 16, 2017

Related U.S. Application Data (60) Provisional application No. 62/027,888, filed on Jul. 23, 2014, provisional application No. 61/979,783, filed on Apr. 15, 2014.

(51) Int. Cl.
C12N 9/10 (2006.01)
C12N 15/82 (2006.01)

(52) U.S. Cl.
CPC ....... *C12N 9/1025* (2013.01); *C12N 15/8212* (2013.01); *C12N 15/8242* (2013.01); *C12Y 203/00* (2013.01)

(58) Field of Classification Search
CPC .................................................. C12N 9/1025
See application file for complete search history.

(56) References Cited

U.S. PATENT DOCUMENTS 8,747,835 B1 * 6/2014 Krichevsky ........ C12N 15/8212
424/93.2

OTHER PUBLICATIONS

Lee, C. et al., Eur. J. Biochem. (1991) vol. 201, pp. 161-167.*
Ast J.C., et al.; J. Bacteriol. 189:6148-6158(2007).*

* cited by examiner

*Primary Examiner* — Russell Kallis
(74) *Attorney, Agent, or Firm* — Dennis A. Bennett (57) ABSTRACT The present disclosure relates to mutated genes of the LUX operon and their use in producing autoluminescent plants and bacteria exhibiting improved light output.

14 Claims, 1 Drawing Sheet

MUTATED LUX OPERON SEQUENCES

CROSS REFERENCE TO RELATED APPLICATIONS

This application claims the benefit of priority of U.S. Provisional Application Ser. No. 61/979,783 filed Apr. 15, 2014 and U.S. Provisional Application Ser. No. 62/027,888 filed Jul. 23, 2014, the contents of each which are incorporated herein by reference in its entirety

INCORPORATION BY REFERENCE OF SEQUENCE LISTING IN COMPUTER READABLE FORM

The sequence listing, which is part of the original disclosure, includes a computer readable form 17.2 KB file entitled "BGL0005_201_US_Seq_Listing_20150415" comprising nucleotide and protein sequences of the present invention submitted via EFS-Web. The subject matter of the Sequence Listing is incorporated herein by reference in its entirety

BACKGROUND OF THE INVENTION

The present disclosure relates to mutated LUX operon sequences and their use in producing autoluminescent glowing plants exhibiting improved light output.

Artificial and synthetic DNA sequences have gained extensive use with development of the field of biology in the past decade. The present disclosure relates to use of artificial nucleotide sequences in the field of bioluminescence, which is emission of light by living organisms. Bioluminescence of bacterial organisms is mediated by the bacterial LUX operon. The LUX operon encodes for the bacterial luciferase, the light emitting enzyme, as well as enzymes responsible for synthesis of luciferins, substrates required for the light emission reaction. The operon contains genes C-D-A-B-E(-G), where Lux A and Lux B code for the components of the luciferase and Lux C, D and E code for a fatty acid reductase complex producing an aldehyde necessary for the reaction. LuxG codes for an enzyme thought to participate in the turnover of the second luciferin, the flavin mononucleotide.

In biotechnology, genes of the LUX operon have a wide range of applications. For instance, the LUX operon is utilized as a reporter in a variety of bacterial and plant biosensors. Bacterial cells of naturally non-glowing species such as *E. coli* have been engineered to contain the LUX operon inducible by pre-determined classes of chemicals. These cells start glowing in the presence of these specific compounds, reporting on the composition or toxicity of the sample. Plants engineered with a fully functional LUX operon have been contemplated for use as phytosensors, monitoring the conditions of the plant and the environment.

In a further application of LUX technology, the present inventor developed the world's first autoluminescent glowing plants by employing genes of the LUX operon (Krichevsky et al. (2010) "Autoluminescent Plants", PLoS One 12; 5(11)e15461; PCT International Publications WO 2009/017821 and WO 2011/106001). During the ensuing years, he has worked to improve the light output of the original autoluminescent plants, and has produced and successfully commercialized the first ornamental glowing plant varieties, demonstrating market interest in glowing plants produced via this technology.

The U.S. ornamentals market was sized at approximately $21 B in the early 2000's, and the entire worldwide market for ornamental plants has been estimated to be over $100 B.

The ornamental plant market is driven by innovation, where outdated varieties are inevitably replaced by new types of plants and flowers. New colors of roses and carnations, and new shapes and colors of petunias, find their way to the marketplace every year. Generation of new and esthetically pleasing varieties is known to be the key force driving the floriculture industry and stimulating its growth.

The inventor's previous application, U.S. Ser. No. 13/901,339, describes novel LUX operon sequences and mutations facilitating enhancement of light output compared to the use of native LUX operon sequences.

In view of the demand from consumers for even brighter glowing plants, further enhancements of LUX gene technology are needed.

SUMMARY OF THE DISCLOSURE

The present disclosure addresses this problem by providing an additional, novel LUX gene mutation, $LuxD^{977Thr \rightarrow Ala}$, neither disclosed nor suggested in the art, which further enhances LUX operon light emission in transgenic plants and bacteria.

Among its many embodiments, the present disclosure encompasses:

A nucleic acid construct, comprising the nucleotide sequences shown in SEQ ID NOs:1-3, SEQ ID NO: 5, and SEQ ID NO: 8, operably linked for expression.

A nucleic acid construct, comprising the nucleotide sequences shown in SEQ ID NOs:1-3, SEQ ID NO: 5, SEQ ID NO: 6, and SEQ ID NO: 8, operably linked for expression.

A nucleic acid construct, comprising the nucleotide sequences shown in SEQ ID NOs:1-3, SEQ ID NOs: 5-7, and SEQ ID NO: 8 operably linked for expression.

The nucleic acid construct of any one of previous disclosed constructs, further comprising the nucleotide sequence shown in SEQ ID NO: 11 operably linked for expression.

A mutated LuxD protein, comprising the amino acid sequence SEQ ID NO: 10.

A mutated LuxD nucleic acid sequence, comprising the nucleic acid sequence SEQ ID NO: 8.

An expression cassette, comprising any one or more of the nucleotide acid constructs disclosed herein.

An expression vector comprising any one or more of the nucleotide acid constructs disclosed herein.

A living cell, comprising the nucleic acid construct of any one of the nucleic acid constructs disclosed herein, a mutated LuxD nucleic acid sequence, in an expression cassette or expression vector comprising one or more of the nucleotide acid constructs disclosed herein.

A living cell which is selected from the group of a bacterial cell or a plant cell.

A living cell which is autoluminescent.

A transgenic plant, comprising the nucleic acid construct of any one of the nucleic acid constructs disclosed herein, a mutated LuxD nucleic acid sequence, in an expression cassette or expression vector comprising one or more of the nucleotide acid constructs disclosed herein.

The transgenic plant of previously embodiments described herein, wherein the nucleic acid construct, mutated LuxD protein, nucleotide sequence, expression cassette, or expression vector is located in a plastid.

The transgenic plant of previously embodiments described herein, wherein the plastid is a chloroplast.

The transgenic plant of previously embodiments described herein, wherein the nucleotide sequences are expressed.

The transgenic plant of previously embodiments described herein, which is autoluminescent.

Plant progeny of previously embodiments described herein.

The progeny of previously embodiments described herein, which are produced sexually or asexually.

The progeny of previously embodiments described herein, which are produced asexually from cuttings.

A part of said plant or progeny of any one of previous embodiments described herein.

The part of said plant or progeny of previous embodiments described herein, which is selected from the group consisting of a protoplast, a cell, a tissue, an organ, a cutting, and an explant.

The part of said plant or progeny of previous embodiments described herein, which is selected from the group consisting of an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

A method of producing an autoluminescent plant, comprising sexually or asexually propagating the plant or progeny of any one of previous embodiments described herein.

A method of producing an autoluminescent plant, comprising asexually propagating the plant or progeny of any one of previous embodiments described herein.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other aspects, features, and advantages of the present disclosure will be better understood from the following detailed descriptions taken in conjunction with the accompanying drawings, all of which are given by way of illustration only, and are not limitative of the presently disclosed embodiments, in which.

REPRESENTATIVE NUCLEOTIDE AND AMINO ACID SEQUENCES

SEQ ID NO:1: artificial Lux A nucleotide sequence;
SEQ ID NO:2: artificial Lux B nucleotide sequence;
SEQ ID NO:3: artificial Lux C nucleotide sequence, incorporating Ala→Gly mutation at amino acid position 389;
SEQ ID NO:4: artificial Lux D nucleotide sequence;
SEQ ID NO:5: artificial Lux E nucleotide sequence, incorporating Gln→Glu mutation at amino acid position 167;
SEQ ID NO:6: artificial Lux G nucleotide sequence;
SEQ ID NO:7: artificial *E. coli* Fre nucleotide sequence;
SEQ ID NO:8: mutated artificial LuxD nucleotide sequence, incorporating Thr→Ala coding mutation at amino acid position 97 ($LuxD^{97Thr \rightarrow Ala}$);
SEQ ID NO:9: amino acid sequence of LuxD prior to mutation (translated from SEQ ID NO:4); a *Photobacterium leiognathi* LuxD protein.
SEQ ID NO:10: amino acid sequence of LuxD, incorporating Thr→Ala mutation at amino acid position 97; a mutated *Photobacterium leiognathi* LuxD protein.
SEQ ID NO:11: artificial *V. fischeri* Yellow Fluorescent Protein nucleotide sequence.

Although not listed above in every case, the present invention also encompasses the amino acid sequences of the proteins encoded by the nucleotide sequences listed. Such amino acid sequences can be deduced by, for example, conventional bioinformatics methods, including the use of publicly available and proprietary computer programs designed for this purpose.

DETAILED DESCRIPTION OF THE DISCLOSURE

The following detailed description is provided to aid those skilled in the art in practicing the various embodiments of the present disclosure described herein, including all the methods, uses, compositions, etc., described herein. Even so, the following detailed description should not be construed to unduly limit the present disclosure, as modifications and variations in the embodiments herein discussed may be made by those of ordinary skill in the art without departing from the spirit or scope of the present inventive discoveries.

The contents of all publications, patent applications, patents, and other references mentioned herein are incorporated by reference herein in their entirety.

Any feature, or combination of features, described herein is(are) included within the scope of the present disclosure, provided that the features included in any such combination are not mutually inconsistent as will be apparent from the context, this specification, and the knowledge of one of ordinary skill in the art. Additional advantages and aspects of the present disclosure are apparent in the following detailed description and claims.

LUX Nucleotide and Amino Acid Sequences

The LUX nucleotide sequences disclosed herein are isolated, purified, non-genomic nucleotide sequences, and include synthetically produced LUX DNA sequences including, for example, those made by chemical oligonucleotide synthesis, enzymatic synthesis, or by recombinant methods, including, for example, cDNA, codon-optimized sequences for efficient expression in different transgenic plants reflecting the pattern of codon usage in such plants, nucleotide sequences that differ from the nucleotide sequences disclosed herein due to the degeneracy of the genetic code but that still encode the LUX protein sequences disclosed herein, nucleotide sequences encoding the presently disclosed LUX proteins comprising conservative (or non-conservative) amino acid substitutions that do not adversely affect their normal activity in contributing to the generation of LUX operon light emission, PCR-amplified nucleotide sequences, and other non-genomic forms of nucleotide sequences familiar to those of ordinary skill in the art.

The LUX amino acid sequences disclosed herein can also be isolated, purified, sequences, or amino acid sequences encoded by and expressed from the present nucleotide sequences, and therefore present in cells in which they are expressed.

The LUX nucleotide and amino acid sequences encompassed by the present disclosure and claims can comprise, consist essentially of, or consist of, the sequences disclosed herein. The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the disclosure necessarily includes the listed ingredients, and is open to unlisted ingredients that do not materially affect the basic and novel properties of the disclosure. A "consisting essentially of" claim occupies a middle ground between closed claims that are written in a closed "consisting of" format and fully open claims that are drafted in a "comprising' format". These terms can be used interchangeably herein if, and when, this may become necessary.

Furthermore, the use of the terms "including", "containing", as well as other related forms, such as "includes" and "included", etc., is not limiting.

Methods and techniques for generating transgenic, transplastomic, and otherwise genetically modified cells and plants are well known in the art.

Overview

The use of native LUX genes to produce autoluminescent plants has been previously described in the art. Patent applications by Krichevsky, i.e., WO 2009/017821 and WO 2011/106001, disclose the use of naturally occurring LUX genes in the form of an operon in plastids, and U.S. Pat. No. 7,663,022 by Hudkins prophetically contemplates nuclear expression of LUX genes from separate vectors. Further, Krichevsky discloses artificial and mutated LUX operon sequences in U.S. Ser. No. 13/901,339, providing for LUX operons with improved light emission properties. However, none of these references either discloses or suggests the mutated LuxD nucleotide or amino acid sequences disclosed in the present application (SEQ ID NOs:8 and 10, respectively), which further improve light emission of the LUX operon.

In one embodiment, LUX operon genes are used in variety of biotechnology applications which can further benefit from enhancement of light output generated by the LUX operon. For example, the problem of further improving and enhancing the light output of the autoluminescent plants, producing brighter glowing ornamental plants which are more appealing and attractive to the consumer, is solved by the mutated DNA sequences of the present disclosure. Expression of these sequences, or combinations thereof, results in autoluminescence produced by a cell that is several fold brighter than that produced by expressing previously known LUX sequences.

Examples of useful combinations of the artificial and mutated sequences disclosed herein include, but are not limited to, SEQ ID NOs:1-3, 5, and 8 in combination; SEQ ID NOs:1-3, 5, 6, and 8 in combination; or SEQ ID NOs:1-3, 5-7, and 8 in combination. In each of these cases, the nucleotide sequences are operably linked for expression. Each of these combinations can further comprise SEQ ID NO:11, i.e., artificial *V. fischeri* Yellow Fluorescent Protein nucleotide sequence, operably linked for expression.

One skilled in the art will recognize that the individual sequences disclosed herein can be used in combination, as indicated above, in any order, and are independent of one another.

As used herein, the phrase "operably linked for expression" and the like encompasses nucleic acid sequences linked in the 5' to 3' direction in such a way as to facilitate expression of an included nucleotide coding sequence.

The singular terms "a", "an", and "the" include plural referents unless context clearly indicates otherwise. Thus for example, reference to a plant, a cell of which contains the nucleic acid construct, expression cassette, expression vector, or nucleotide sequences of any one of the embodiments listed above, includes plants containing one or more such cells.

Similarly, the word "or" is intended to include "and" unless the context clearly indicates otherwise. Hence, comprising A or B means including A, or B, or A and B.

Methods

Practice of the embodiments encompassed by the present disclosure employs, unless otherwise indicated, conventional techniques of molecular biology, recombinant DNA technology, microbiology, chemistry, etc., which are well known in the art and within the capabilities of those of ordinary skill in the art. Such techniques include the following non-limiting examples: preparation of cellular, plasmid, and bacteriophage DNA; manipulation of purified DNA using nucleases, ligases, polymerases, and DNA-modifying enzymes; introduction of DNA into living cells; cloning vectors for various organisms; PCR; gene deletion, modification, replacement, or inhibition; production of recombinant peptides, polypeptides, and proteins in host cells; chromatographic methods; etc.

Such methods are well known in the art and are described, for example, in Green and Sambrook (2012) *Molecular Cloning: A Laboratory Manual*, Fourth Edition, Cold Spring Harbor Laboratory Press; Ausubel et al. (2003 and periodic supplements) *Current Protocols in Molecular Biology*, John Wiley & Sons, New York, N.Y.; Roe et al. (1996) *DNA Isolation and Sequencing: Essential Techniques*, John Wiley & Sons; M. J. Gait (Editor) (1984) *Oligonucleotide Synthesis: A Practical Approach*, IRL Press; D. M. J. Lilley and J. E. Dahlberg (1992) *Methods in Enzymology: DNA Structure Part A: Synthesis and Physical Analysis of DNA*, Academic Press; and *Lab Ref: A Handbook of Recipes, Reagents, and Other Reference Tools for Use at the Bench*, Edited by Jane Roskams and Linda Rodgers (2002) Cold Spring Harbor Laboratory Press.

Methods and techniques for the production of transgenic, transplastomic, autoluminescent plants are disclosed in Krichevsky et al. (2010) "Autoluminescent Plants", PLoS One 12; 5(11)e15461; and PCT International Publications WO 2009/017821 and WO 2011/106001.

The entire contents of each of the foregoing texts and patent documents is herein incorporated by reference.

The following example is meant to be illustrative, and not limiting, of the practice or products of the present disclosure.

EXAMPLES

Example 1

Enhanced Light Emission in *E. coli* Expressing a Mutated LuxD Sequence

Disclosed herein is a structural mutation in the LuxD gene, leading to enhanced light emission of the LUX operon. Specifically, light emission catalyzed by an expression cassette comprising SEQ ID NOs:1-7, previously described in U.S. application Ser. No. 13/901,339, is further enhanced if LuxD (SEQ ID NO:4) is further mutated at amino acid position 97 by replacing threonine (Thr(T)) with alanine (Ala(A)), i.e., (LuxD$^{97T \to A}$).

Methods for nucleic acid mutagenesis are known in the art (e.g., Chen et al. (2002) "Site-directed mutagenesis mediated by a single polymerase chain reaction product." *Methods Mol. Biol.* 182:67-70). Methods for transforming *E. coli* are well known in the art.

LuxD Mutation

The threonine residue at amino acid position 97 in LuxD subject to mutation is shown underlined, in bold, in 16 point type, in the amino acid sequence below: SEQ ID NO: 9 describes the LuxD amino acid sequence prior to light-enhancing mutation (translated from SEQ ID NO:4, artificial Lux D nucleotide sequence): MENTQHSLPIDHVIDIGD-NRYIRVWETKPKNKETKRNNTIVIASGFARRMDHF AGLAEYLANNGFRVIRYDSLNHVGLSSGEIKQFSMS-VGKHSLLTVIDWLKER NINNIGLIASSLSARI-AYEVAAEIDLSFLITAVGVVNLRSTLEKALKY-DYLQME VNTIPEDLIFEGHNLGSKVFVTDCFENNWDSLDSTIN-KICELDIPFIAFTSDGDD WVCQHEVKHLVSNVKSDK-KKIYSLVGSSHDLGENLVVLRNFYQSMTKAAVS LDRQLVELVDEREPNFEDLTVITVNERRLKNKIENEI-INRLADRVLASV SEQ ID NO: 10 shows the amino acid sequence of mutated LuxD with the alanine substitution at amino acid residue 97.

Enhanced Light Emission

Figure 1:
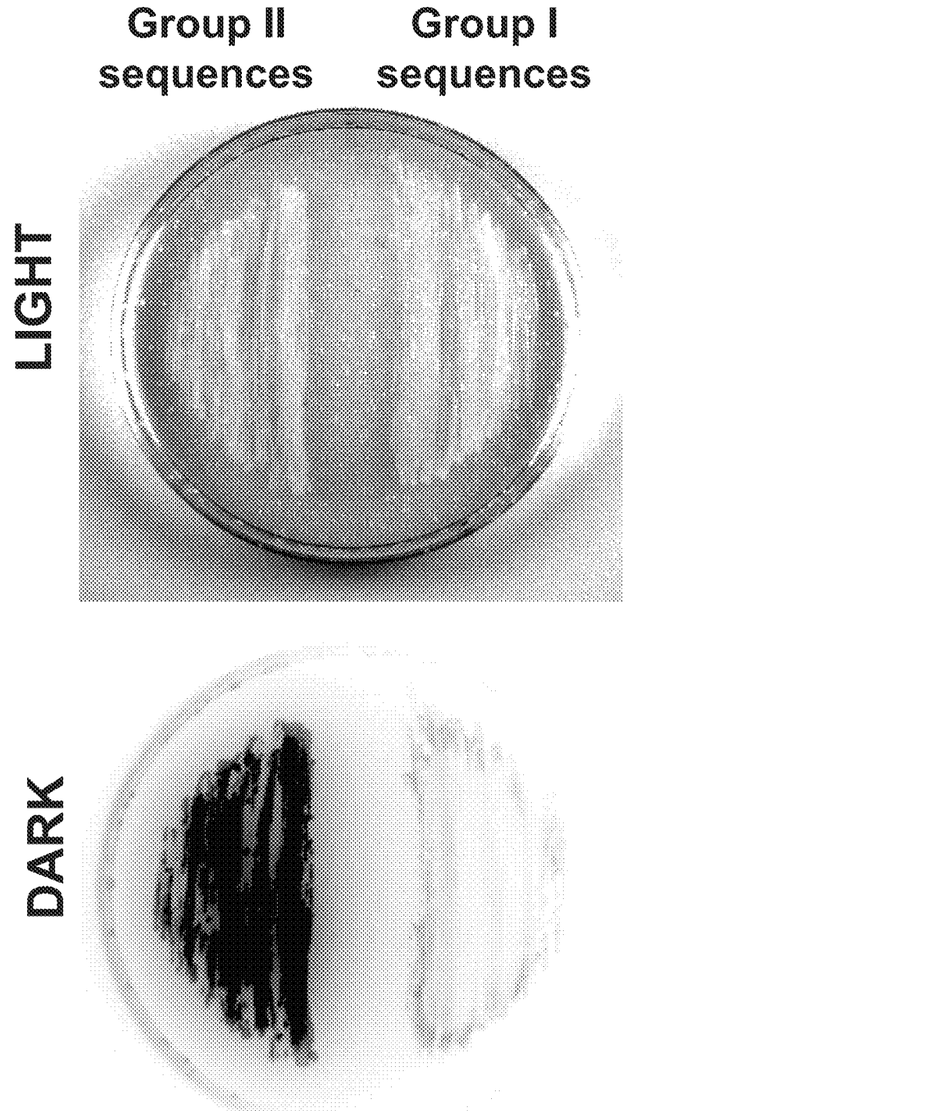
FIG. 1 shows an image of light emission of *E. coli* cells expressing DNA sequences SEQ ID NOs:1-7 (Group I Sequences, right), disclosed in the inventor's previous application U.S. Ser. No. 13/901,339, compared to that in cells expressing SEQ ID NOs: 1-3 and 5-7, and mutated LuxD sequence SEQ ID NO:8 (Group II Sequences, left), disclosed herein for the first time. For comparison purposes, *E. coli* cultures expressing the two groups of sequences were imaged using a ChemiDoc XRS Molecular Imager (Bio-Rad). The top panel is a photograph of the plate in the light ("LIGHT"); the bottom panel is a negative showing the comparative light emission in the dark ("DARK").

FIG. 1 shows an image of light emission of *E. coli* cells expressing nucleotide sequences SEQ ID NOs: 1-7 (Group I Sequences, on the right), disclosed in the inventor's previous application U.S. Ser. No. 13/901,339 compared to that in cells expressing sequences SEQ ID NOs: 1-3, 5-7, and mutated LuxD$^{97Thr \to Ala}$ (SEQ ID NO:8) disclosed herein for the first time (Group II Sequences, on the left). Comparison of light emission from both transformed *E. coli* cultures was performed by imaging the streaked cells using a ChemiDoc XRS Molecular Imager (Bio-Rad). The top panel shows a photograph of the plate in the light (LIGHT). The lower panel is a negative showing the comparative light emission of cells on the plate in the dark (DARK).

The results shown in FIG. 1 clearly demonstrate that substitution of threonine at amino acid position 97 in LuxD with alanine by expressing SEQ ID NO:8 in combination with the other Lux nucleotide sequences significantly enhances light emission when included in a LUX operon.

In view of these results, it is fully expected that use of an artificial nucleotide sequence encoding LuxD comprising the Thr→Ala mutation at amino acid position 97, e.g., SEQ ID NO: 8 or an equivalent, in combination with the other artificial LUX operon sequences disclosed herein, will produce a similar, significant light-enhancing effect in plants.

As noted above, the artificial, non-genomic LUX nucleotide sequences disclosed herein include, for example, synthetically produced LUX DNA sequences made by, for example, chemical oligonucleotide synthesis, enzymatic synthesis, or by recombinant methods, and include for example, cDNA, codon-optimized sequences for efficient expression in different transgenic plants reflecting the pattern of codon usage in such plants, nucleotide sequences that differ from the nucleotide sequences disclosed herein due to the degeneracy of the genetic code but that still encode the LUX protein sequences disclosed herein, nucleotide sequences encoding the presently disclosed LUX proteins comprising conservative (or non-conservative) amino acid substitutions that do not adversely affect their normal activity in generating light emission, PCR-amplified nucleotide sequences, and other non-genomic forms of nucleotide sequences familiar to those of ordinary skill in the art.

Useful Plastid Targets

The plastids of higher plants are an attractive target for genetic engineering to produce autoluminescent plants. The artificial DNA sequences disclosed herein can be expressed in a variety of different plastids, including chloroplasts, chromoplasts, etioplasts, gerontoplasts, leucoplasts, proplastids, amyloplasts, elaioplasts, etc. In one embodiment, the plastid is a chloroplast or a chromoplast. Chromoplasts can be present in leaves, as well as in flower petals or bracts such as those found in poinsettias.

Applications of the Technology

Besides applications in ornamental plants, where bright autoluminescent plants suitable for the ornamental industry are attractive to consumers, the present sequences have utility in producing highly effective bacterial and plant biosensors (phytosensors) emitting light in response to various types of stress or other conditions when operons containing these sequences are under the control of appropriate environment-responsive promoters, e.g., stress-inducible promoters, and are thus useful in agriculture for crop or environmental monitoring, as well as in basic research.

In additional examples, the presently disclosed sequences are further useful in generating more efficient plant research systems, where their autoluminescent properties can be used as a reporter system for gene expression and other scientific assays.

Plants

Plants encompassed by the present invention comprise one or more cells containing the nucleotide sequences, constructs, expression cassettes, expression vectors, or amino acid sequences disclosed herein, and include both monocots and dicots, ornamentals as well as crop plants. Non-limiting examples include ornamental plants such as petunias, poinsettias, ornamental tobacco, roses, carnations, calibrachoa, orchids, begonias, kalanchoes, African violets, hostas, elephant ears, cacti and other succulents, geraniums, snapdragons, gesneriads, irises, gerberas, gladioli, tulips, heucheras, ivies, chrysanthemums, ornamental grasses and turf grasses, as well as crop plants such as corn and oil producing palms. Tissue culture and biolistic procedures involved in the transformation process are well known in the art.

Plant Parts and Progeny

The present application encompasses all plants described herein, as well as all plants resulting from such plants and their seeds, including, for example, all plant parts, materials (including propagation materials), germplasm, cuttings, divisions, propagations, derivatives, progeny (including hybrids), clones, samples, seeds, and harvested material thereof.

Parts of plants encompassed by the present disclosure include, for example, a protoplast, a cell, a tissue, an organ, a cutting, an explant, a reproductive tissue, a vegetative tissue, and a biomass. Such parts further include an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

The present invention also encompasses progeny, whether produced sexually or asexually, of transgsenic plants of the invention containing sequences disclosed herein.

Methods of Plant Propagation

In regard to methods of propagating autoluminescent plants encompassed by the present invention, methods of propagation and reproduction of such plants are well known in the art, and include both sexual and asexual techniques.

Asexual reproduction is the propagation of a plant to multiply the plant without the use of seeds to assure an exact genetic copy of the plant being reproduced.

Any known method of asexual reproduction which renders a true genetic copy of the plant may be employed in the present invention. Acceptable modes of asexual reproduction include, but are not limited to, rooting cuttings; grafting; explants; budding; apomictic seeds; bulbs; division; slips; layering; rhizomes; runners; corms; tissue culture; nucellar embryos; and any other conventional method of asexual propagation. The present invention encompasses all such methods of propagation and reproduction of plants encompassed by the present invention.

Various embodiments of the present disclosure being thus described, it will be obvious that the same can be varied in many ways. Such variations are not to be regarded as a departure from the spirit and scope of the disclosure, and all such modifications as would be obvious to one skilled in the art are intended to be included within the scope of the following claims.

| Nucleotide and Amino Acid Sequences |
|---|
| SEQ ID NO: 1 |
| ATGAAAATAAGTAATATTTGTTTCTCATATCAACCACCAGGGGAGTCC |
| CATCAGGAGGTTATGGAAAGGTTTATACGACTAGGTGTCGCATCTGAA |
| GAATTAAATTTTGATGGATTTTATACTTTAGAGCACCATTTTACCGAA |
| TTTGGAATAACTGGTAATTTATATATTGCATGTGCAAACATACTAGGA |
| CGAACTAAGCGTATTCAAGTTGGCACAATGGGCATAGTTCTTCCTACA |
| GAGCATCCGGCTCGACATGTAGAATCACTACTTGTTCTTGATCAATTG |
| TCTAAGGGTAGATTTAATTATGGAACGGTTAGGGGTTTGTATCATAAG |
| GATTTTCGAGTGTTTGGGACATCCCAGGAGGATTCCCGAAAAACAGCA |
| GAAAATTTCTATTCTATGATTTTAGATGCGTCCAAGACCGGAGTGTTG |
| CATACGGACGGGGAGGTAGTAGAATTTCCTGATGTGAATGTCTACCCA |
| GAAGCCTATTCTAAAAAGCAGCCTACTTGTATGACTGCGGAATCTTCT |
| GAGACTATTACTTATTTAGCGGAAAGAGGGCTACCTATGGTGTTAAGT |

| Nucleotide and Amino Acid Sequences |
|---|
| TGGATTATCCCAGTTAGTGAAAAAGTATCTCAAATGGAGTTATATAAT |
| GAAGTGGCCGCTGAACATGGGCATGATATAAACAATATTGAACACATT |
| CTAACATTTATTTGCTCTGTTAATGAAGATGGGGAGAAAGCCGATAGT |
| GTATGTAGGAATTTTTTGGAGAATTGGTATGACTCCTACAAGAATGCC |
| ACAAACATCTTTAATGATTCCAACCAAACAAGAGGTTATGATTATTTA |
| AAAGCTCAATGGCGAGAGTGGGTTATGAAAGGTTTAGCTGACCCACGA |
| AGGCGTCTTGATTATTCTAATGAATTAAATCCGGTCGGTACACCTGAA |
| CGTTGTATCGAAATTATTCAAAGTAATATTGATGCAACCGGGATAAAA |
| CACATTACCGTGGGCTTTGAAGCTAATGGTAGTGAACAGGAAATTAGA |
| GAATCTATGGAACTTTTTATGGAAAAAGTTGCACCGCATCTTAAAGAT |
| CCCCAATAA |
| SEQ ID NO: 2 |
| ATGAACTTTGGATTGTTTTTCCTAAATTTCCAACCAGAAGGAATGACT |
| TCCGAAATGGTACTAGATAATATGGTTGATACAGTAGCATTGGTAGAC |
| AAAGATGACTATCATTTCAAGCGTGTATTGGTGTCTGAACATCATTTC |
| TCCAAAAATGGCATTATAGGGGAGCCCTTAACCGCTATATCTTTCCTT |
| TTAGGTCTAACCAAGAGAATAGAAATAGGTTCTTTGAATCAGGTTATA |
| ACGACCCACCATCCTGTAAGAATTGGCGAACAGACTGGATTATTAGAT |
| CAGATGTCTTACGGTCGTTTCGTTTTAGGTTTATCAGATTGCGTTAAT |
| GATTTCGAAATGGATTTTTTAAACGAAAACGTAGTTCACAACAACAA |
| CAATTCGAAGCATGTTATGAAATTTTAAATGAAGCCTTAACTACGAAT |
| TATTGCCAAGCGGATGATGATTTTTTCAATTTTCCGAGGATCAGTGTA |
| AATCCCCATTGTATCTCTGAGGTTAAACAATACATTTTGGCATCTTCT |
| ATGGGTGTAGTTGAATGGGCCGCTCGAAAAGGTCTTCCTTTAACGTAT |
| AGATGGAGTGATAGTTTAGCAGAAAAAGAGAAGTATTATCAGCGTTAC |
| TTAGCGGTTGCTAAAGAGAACAATATAGATGTTTCAAATATCGATCAT |
| CAATTTCCTCTTCTTGTAAATATTAACGAAAATCGAAGAATAGCACGA |
| GATGAAGTACGTGAGTACATTCAGAGTTATGTATCAGAAGCCTATCCC |
| ACTGACCCTAATATTGAACTTCGTGTAGAAGAATTGATCGAACAACAC |
| GCAGTCGGGAAAGTCGATGAATATTATGATTCTACGATGCACGCTGTC |
| AAAGTTACTGGTTCTAAAAATTTATTATTATCTTTTGAATCTATGAAA |
| AATAAAGATGACGTCACTAAACTTATCAACATGTTCAACCAAAAAATC |
| AAGGATAACTTAATAAAGTGA |
| SEQ ID NO: 3 |
| ATGATCAAAAAAATCCCTATGATAATTGGGGAGTAGTCCAGAACACA |
| TCCGGTTATGGAATGAGAGAATTAACATTAAACAATAATAAAGTTAAC |
| ATTCCAATTATCACACAAAGTGATGTAGAAGCTATTCAATCTCTAAAT |
| ATTGAGAACAAATTGACAATAAATCAGATTGTAAATTTCCTTTATACT |
| GTAGGCCAAAAATGGAAATCTGAGACGTATAGTCGTCGATTAACTTAT |

| Nucleotide and Amino Acid Sequences |
|---|
| ATCAGAGATTTAATCAAATTCTTAGGTTATAGTCAGGAAATGGCTAAA |
| TTGGAAGCTAATTGGATTAGTATGATATTATGTTCTAAAAGTGCTTTA |
| TATGACATAGTAGAAAATGATTTAAGTAGTCGTCATATCATTGATGAA |
| TGGATTCCCCAAGGTGAATGCTATGTAAAAGCATTGCCTAAGGGTAAG |
| TCCGTACACTTGTTAGCAGGAAATGTTCCTTTATCAGGAGTAACCTCC |
| ATACTAAGAGCAATTCTTACAAAAAATGAATGCATTATTAAAACTAGT |
| TCAGCAGACCCATTTACTGCCACTGCACTTGTTAACTCTTTTATAGAC |
| GTTGATGCCGAACATCCTATAACACGATCCATTAGTGTAATGTATTGG |
| TCCCATTCTGAAGATTTAGCAATTCCCAAACAAATAATGTCTTGTGCT |
| GACGTTGTTATAGCATGGGGAGGGGACGATGCAATAAAATGGGCAACT |
| GAACATGCACCTTCTCACGCAGACATATTGAAATTCGGACCGAAAAAA |
| TCCATTTCCATTGTCGATAATCCTACGGATATTAAGGCAGCTGCTATC |
| GGAGTGGCTCATGACATTTGTTTTTATGATCAGCAAGCATGCTTCTCA |
| ACCCAAGATATATATTATATCGGAGATTCAATTGATATTTTCTTTGAT |
| GAATTAGCTCAACAGTTAAATAAATATAAAGACATTTTACCTAAAGGG |
| GAACGAAATTTCGATGAGAAGGCAGCTTTCTCCCTTACTGAAAGAGAG |
| TGTCTTTTCGCAAAATATAAAGTTCAAAAAGGTGAATCCCAATCTTGG |
| TTGCTTACCCAAAGTCCAGCGGGAAGTTTGGAAATCAACCTTTGAGT |
| CGTTCTGCGTATATTCATCAGGTAAATGATATAAGTGAAGTAATACCC |
| TTCGTACATAAAGGAGTTACTCAAACTGTAGCTATCGCGCCTTGGGAA |
| TCAAGTTTTAAATACAGAGATATTTTGGCTGAGCATGGTGCTGAGCGT |
| ATCATTGAAGCAGGAATGAATAACATTTTTCGTGTAGGAGGTGCCCAC |
| GATGGGATGCGACCCTTGCAACGTTTGGTTAATTATATTTCTCATGAA |
| CGTCCTAGTACATATACAACAAAAGATGTTAGTGTAAAAATAGAACAG |
| ACAAGGTATCTTGAAGAAGATAAATTCTTAGTTTTTGTACCGTAG |
| SEQ ID NO: 4 |
| ATGGAAAATACACAACATAGTTTACCTATTGATCACGTAATCGACATA |
| GGTGACAACCGTTACATCAGGGTGTGGGAAACTAAACCTAAAAACAAA |
| GAAACTAAAAGAAATAATACCATAGTGATAGCGTCCGGTTTTGCAAGA |
| AGAATGGATCACTTTGCTGGATTAGCTGAATATCTTGCCAACAATGGA |
| TTCCGAGTTATTAGATACGATTCACTAAATCATGTGGGCTTGTCTAGT |
| GGTGAAATTAAACAGTTTAGTATGTCTGTAGGTAAACATTCTTTGCTA |
| ACGGTAATTGATTGGCTTAAAGAACGAAATATCAACAATATTGGACTA |
| ATTGCAAGTTCCTTAAGTGCCCGTATAGCCTATGAAGTAGCCGCAGAA |
| ATTGATTTATCCTTCCTTATAACAGCAGTTGGGGTTGTGAATTTACGT |
| TCTACTCTTGAAAAAGCACTTAAATATGATTATTTGCAGATGGAAGTC |
| AATACGATTCCTGAAGACTTAATATTTGAAGGGCATAATCTAGGTTCA |
| AAAGTTTTTGTGACTGATTGTTTGAAAACAACTGGGATTCTTTAGAC |
| TCAACTATTAATAAAATTTGTGAGCTTGATATTCCGTTCATAGCTTTC |

| Nucleotide and Amino Acid Sequences |
|---|
| ACTTCTGATGGGGATGATTGGGTTTGTCAACATGAAGTAAAACACCTA |
| GTGTCCAATGTAAAATCTGACAAAAAAAAGATATACTCTTTAGTTGGT |
| AGTTCCCATGATTTGGGGGAAATTTGGTCGTTTTACGAAATTTCTAT |
| CAAAGTATGACTAAAGCTGCTGTCTCATTGGATAGGCAATTGGTTGAA |
| TTAGTTGATGAAATCATAGAACCAAATTTTGAGGATTTAACCGTAATT |
| ACAGTCAATGAAAGAAGACTTAAAAATAAAATAGAAAATGAAATAATA |
| AACAGACTAGCAGATCGAGTTCTTGCTTCCGTATAA |
| SEQ ID NO: 5 |
| ATGTCCACCTTACTAAACATCGATGCAACGGAGATTAAAGTTAGTACC |
| GAGATAGATGATATAATCTTTACAAGTAGTCCATTAACTTTATTATTT |
| GAAGATCAAGAAAAAATTCAGAAAGAATTAATACTTGAAAGTTTTCAT |
| TATCATTATAACCATAATAAAGATTACAAGTATTATTGTAATATTCAG |
| GGGGTTGATGAGAACATTCAATCAATTGACGACATTCCAGTATTTCCT |
| ACATCCATGTTTAAATACTCTCGTCTTCATACAGCCGATGAGAGTAAT |
| ATAGAAAATTGGTTTACATCATCCGGTACTAAAGGCGTTAAGTCTCAT |
| ATTGCTAGGGATAGGCAGTCAATTGAAAGATTACTAGGATCAGTTAAT |
| TATGGTATGAAATATCTTGGAGAATTTCATGAACATCAACTTGAACTT |
| GTAAATATGGGACCAGATCGTTTTTCCGCTTCAAACGTGTGGTTCAAA |
| TATGTTATGAGTTTAGTAGAATTGTTATATCCTACTACTTTTACTGTG |
| GAAAATGATGAGATAGATTTTGAACAAACTATCTTGGCTTTAAAAGCG |
| ATACAACGAAAAGGAAAAGGAATATGTTTAATAGGACCGCCTTATTTT |
| ATATACTTGTTATGCCATTATATGAAAGAACATAATATAGAATTTAAT |
| GCAGGGGCTCACATGTTTATTATTACGGGAGGGGGATGGAAAACAAAA |
| CAAAAAGAGGCGTTAAATAGGCAAGATTTCAATCAACTTCTTATGGAA |
| ACATTCTCCTTATTTCATGAGTCACAAATTAGAGACATATTTAATCAA |
| GTTGAATTGAATACATGTTTCTTCGAAGATTCTCTTCAACGAAAACAT |
| GTGCCACCTTGGGTATATGCTCGTGCATTAGATCCTGTTACTTTGACT |
| CCCGTAGAAGACGGGCAGGAAGGCTTGATGTCTTATATGGACGCCTCC |
| AGTACATCATATCCGACTTTCATCGTTACGGATGATATTGGCATTGTA |
| AGGCATCTAAAAGAGCCAGATCCCTTCCAAGGTACAACCGTAGAAATT |
| GTTAGACGTCTTAACACACGAGAGCAAAAGGGTTGTTCTTTATCTATG |
| GCTACAAGTCTTAAATAA |
| SEQ ID NO: 6 |
| ATGATCTTCAACTGTAAAGTCAAAAAAGTTGAAGCATCCGATTCACAT |
| ATTTATAAAGTCTTTATCAAACCCGATAAGTGTTTCGATTTTAAAGCA |
| GGCCAATATGTTATTGTGTACCTAAACGGGAAAAATTTACCATTTAGT |
| ATAGCCAACTGTCCTACATGTAATGAATTATTGGAATTACATGTAGGC |
| GGGTCTGTAAAAGAATCTGCAATTGAAGCAATATCACACTTTATTAAT |
| GCTTTTATATATCAAAAAGAATTTACTATTGATGCTCCGCATGGAGAC |
| GCCTGGTTACGAGATGAGTCTCAATCTCCGCTTTTGTTAATAGCTGGC |

| Nucleotide and Amino Acid Sequences |
|---|
| GGCACAGGTTTATCATATATCAATAGTATTTTAAGTTGCTGCATTTCT |
| AAACAACTATCCCAACCGATCTATTTATACTGGGGTGTCAACAATTGT |
| AACCTTTTGTATGCAGATCAACAATTAAAAACTTTGGCCGCACAATAT |
| CGTAATATTAATTATATCCCTGTAGTTGAGAATCTTAATACAGATTGG |
| CAAGGAAAAATTGGGAATGTAATAGATGCAGTAATCGAAGATTTTAGT |
| GACCTTTCAGATTTCGACATCTATGTTTGTGGACCCTTCGGTATGTCC |
| AGAACAGCTAAAGATATTCTAATTTCACAAAAGAAAGCAAACATAGGG |
| AAGATGTATTCAGATGCTTTTTCTTACACGTGA |

SEQ ID NO: 7
ATGACTACTCTTTCTTGTAAGGTGACATCAGTGGAGGCTATAACTGAC
ACAGTGTACAGAGTTAGAATCGTACCAGATGCAGCATTTAGTTTTAGG
GCCGGTCAATATTTGATGGTTGTAATGGACGAGAGAGATAAGAGACCA
TTCAGCATGGCCTCTACTCCAGATGAGAAAGGGTTTATCGAACTGCAC
ATTGGAGCATCAGAGATCAATTTATACGCAAAAGCAGTCATGGACAGG
ATCTTAAAGGACCATCAGATTGTTGTTGATATTCCTCACGGCGAAGCA
TGGCTTAGGGATGATGAGGAAAGACCTATGATTCTCATCGCTGGCGGA
ACAGGGTTCTCTTACGCTAGGTCTATACTCCTCACCGCCCTAGCACGT
AATCCAAATAGGGATATTACCATTTACTGGGGTGGTAGAAGAGCAG
CACCTTTACGACCTTTGCGAATTGGAGGCCCTTAGCTTAAAGCATCCT
GGTCTACAAGTTGTGCCAGTTGTCGAACAACCTGAGGCAGGATGGAGA
GGGCGTACAGGAACAGTGCTAACTGCCGTTTTACAGGATCATGGCACT
CTTGCTGAGCACGTATTTATATTGCCGGTAGATTCGAAATGGCTAAG
ATTGCACGTGACCTTTTTTGTTCTGAAAGAAATGCCAGGGAAGATAGA
TTGTTCGGTGATGCTTTCGCATTCATTTGA

SEQ ID NO: 8
ATGGAAAATACACAACATAGTTTACCTATTGATCACGTAATCGACATA
GGTGACAACCGTTACATCAGGGTGTGGGAAACTAAACCTAAAAACAAA
GAAACTAAAAGAAATAATACCATAGTGATAGCGTCCGGTTTTGCAAGA
AGAATGGATCACTTTGCTGGATTAGCTGAATATCTTGCCAACAATGGA
TTCCGAGTTATTAGATACGATTCACTAAATCATGTGGGCTTGTCTAGT
GGTGAAATTAAACAGTTTAGTATGTCTGTAGGTAAACATTCTTTGCTA
GCGGTAATTGATTGGCTTAAAGAACGAAATATCAACAATATTGGACTA
ATTGCAAGTTCCTTAAGTGCCCGTATAGCCTATGAAGTAGCCGCAGAA
ATTGATTTATCCTTCCTTATAACAGCAGTTGGGGTTGTGAATTTACGT
TCTACTCTTGAAAAAGCACTTAAATATGATTATTTGCAGATGGAAGTC
AATACGATTCCTGAAGACTTAATATTTGAAGGGCATAATCTAGGTTCA
AAGTTTTTGTGACTGATTGTTTTGAAAACAACTGGGATTCTTTAGAC
TCAACTATTAATAAAATTTGTGAGCTTGATATTCCGTTCATAGCTTTC
ACTTCTGATGGGGATGATTGGGTTTGTCAACATGAAGTAAAACACCTA

SEQ ID NO: (continued)
GTGTCCAATGTAAAATCTGACAAAAAAAAGATATACTCTTTAGTTGGT
AGTTCCCATGATTTGGGGGAAATTTGGTCGTTTTACGAAATTTCTAT
CAAAGTATGACTAAAGCTGCTGTCTCATTGGATAGGCAATTGGTTGAA
TTAGTTGATGAAATCATAGAACCAAATTTTGAGGATTTAACCGTAATT
ACAGTCAATGAAAGAAGACTTAAAAATAAAATAGAAAATGAAATAATA
AACAGACTAGCAGATCGAGTTCTTGCTTCCGTATAA SEQ ID NO: 9
MENTQHSLPIDHVIDIGDNRYIRVWETKPKNKETKRNNTIVIASGFAR
RMDHFAGLAEYLANNGFRVIRYDSLNHVGLSSGEIKQFSMSVGKHSLL
TVIDWLKERNINNIGLIASSLSARIAYEVAAEIDLSFLITAVGVVNLR
STLEKALKYDYLQMEVNTIPEDLIFEGHNLGSKVFVTDCFENNWDSLD
STINKICELDIPFIAFTSDGDDWVCQHEVKHLVSNVKSDKKKIYSLVG
SSHDLGENLVVLRNFYQSMTKAAVSLDRQLVELVDEIIEPNFEDLTVI
TVNERRLKNKIENEIINRLADRVLASV SEQ ID NO: 10
MENTQHSLPIDHVIDIGDNRYIRVWETKPKNKETKRNNTIVIASGFAR
RMDHFAGLAEYLANNGFRVIRYDSLNHVGLSSGEIKQFSMSVGKHSLL
AVIDWLKERNINNIGLIASSLSARIAYEVAAEIDLSFLITAVGVVNLR
STLEKALKYDYLQMEVNTIPEDLIFEGHNLGSKVFVTDCFENNWDSLD
STINKICELDIPFIAFTSDGDDWVCQHEVKHLVSNVKSDKKKIYSLVG
SSHDLGENLVVLRNFYQSMTKAAVSLDRQLVELVDEIIEPNFEDLTVI
TVNERRLKNKIENEIINRLADRVLASV SEQ ID NO: 11
ATGTTTAAAGGAATTGTGGAAGGCATTGGAATCATTGAGAAGATAGAC
ATATATACAGACCTTGACAAGTATGCCATCAGATTCCCTGAAAACATG
TTGAACGGCATTAAAAAAGAGTCTTCCATTATGTTTAACGGCTGCTTT
CTTACAGTGACCAGCGTTAATAGCAACATCGTCTGGTTTGATATTTTT
GAGAAGGAAGCTAGGAAACTGGATACATTTAGAGAATATAAGGTTGGA
GATAGAGTCAATTTGGGTACATTCCCAAAGTTTGGTGCTGCATCTGGA
GGACATATTTTGAGTGCAAGAATATCTTGCGTTGCTAGTATTATTGAG
ATTATAGAGAATGAAGATTATCAACAGATGTGGATTCAGATTCCTGAG
AACTTTACTGAGTTCTTAATTGACAAAGACTATATTGCTGTCGATGGT
ATCTCTTTAACAATCGACACTATAAAAAACAATCAGTTTTTTATTAGT
TTGCCGTTAAAAATAGCTCAAAATACCAACATGAAATGGAGGAAAAAG
GGAGATAAGGTTAACGTGGAGTTGTCTAATAAGATTAACGCTAATCAG
TGTTGGTGA

What is claimed is:

1. A nucleic acid construct, comprising the nucleotide sequences shown in SEQ ID NOs: 1-3, SEQ ID NOs: 5-7, and SEQ ID NOs: 8 wherein the nucleotide sequences are operably linked for expression.

2. The nucleic acid construct of claim 1 further comprising SEQ ID NO: 11 wherein the nucleotide sequences are operably linked for expression.

3. An expression cassette comprising the nucleotide sequences of claim 1.

4. An expression vector comprising the nucleotide sequences of claim 1.

5. A living cell comprising a nucleic acid construct of claim 1.

6. The living cell of claim 5, which is selected from the group consisting of a bacterial cell and a plant cell.

7. The living cell of claim 6, which is autoluminescent.

8. A transgenic plant comprising a nucleic acid construct of claim 1.

9. Progeny of the transgenic plant of claim 8 comprising the nucleotide sequences of claim 1.

10. The progeny of claim 9, wherein the progeny are produced sexually or asexually.

11. The progeny of claim 10, which are produced asexually from cuttings.

12. A plant part of said progeny of claim 11.

13. The plant part of said progeny of claim 12, which is selected from the group consisting of a protoplast, a cell, a tissue, an organ, a cutting, and an explant.

14. The plant part of said progeny of claim 13, which is selected from the group consisting of an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

* * * * *

SEQUENCE LISTING

<160> NUMBER OF SEQ ID NOS: 11

<210> SEQ ID NO 1
<211> LENGTH: 1065
<212> TYPE: DNA
<213> ORGANISM: Artificial Sequence
<220> FEATURE:
<223> OTHER INFORMATION: Artificial Lux A nucleotide sequence

<400> SEQUENCE: 1

| | | | | | |
|---|---|---|---|---|---|
| atgaaaataa | gtaatatttg | tttctcatat | caaccaccag | gggagtccca | tcaggaggtt | 60 |
| atggaaaggt | ttatacgact | aggtgtcgca | tctgaagaat | taaattttga | tggattttat | 120 |
| actttagagc | accattttac | cgaatttgga | ataactggta | atttatatat | tgcatgtgca | 180 |
| aacatactag | gacgaactaa | gcgtattcaa | gttggcacaa | tgggcatagt | tcttcctaca | 240 |
| gagcatccgg | ctcgacatgt | agaatcacta | cttgttcttg | atcaattgtc | taagggtaga | 300 |
| tttaattatg | gaacggttag | gggtttgtat | cataaggatt | ttcgagtgtt | tgggacatcc | 360 |
| caggaggatt | cccgaaaaac | agcagaaaat | ttctattcta | tgattttaga | tgcgtccaag | 420 |
| accggagtgt | tgcatacgga | cggggaggta | gtagaatttc | tgatgtgaa | tgtctaccca | 480 |
| gaagcctatt | ctaaaaagca | gcctacttgt | atgactgcgg | aatcttctga | gactattact | 540 |
| tatttagcgg | aaagagggct | acctatggtg | ttaagttgga | ttatcccagt | tagtgaaaaa | 600 |
| gtatctcaaa | tggagttata | taatgaagtg | gccgctgaac | atgggcatga | tataaacaat | 660 |
| attgaacaca | ttctaacatt | tatttgctct | gttaatgaag | atggggagaa | agccgatagt | 720 |
| gtatgtagga | attttttgga | gaattggtat | gactcctaca | agaatgccac | aaacatcttt | 780 |
| aatgattcca | accaaacaag | aggttatgat | tatttaaaag | ctcaatggcg | agagtgggtt | 840 |
| atgaaaggtt | tagctgaccc | acgaaggcgt | cttgattatt | ctaatgaatt | aaatccggtc | 900 |
| ggtacacctg | aacgttgtat | cgaaattatt | caaagtaata | ttgatgcaac | cgggataaaa | 960 |
| cacattaccg | tgggctttga | agctaatggt | agtgaacagg | aaattagaga | atctatggaa | 1020 |
| cttttatgg | aaaagttgc | accgcatctt | aaagatcccc | aataa | | 1065 |

<210> SEQ ID NO 2
<211> LENGTH: 981
<212> TYPE: DNA
<213> ORGANISM: Artificial Sequence
<220> FEATURE:
<223> OTHER INFORMATION: Artificial Lux B nucleotide sequence

<400> SEQUENCE: 2

| | | | | | |
|---|---|---|---|---|---|
| atgaactttg | gattgttttt | cctaaatttc | caaccagaag | gaatgacttc | cgaaatggta | 60 |
| ctagataata | tggttgatac | agtagcattg | gtagacaaag | atgactatca | tttcaagcgt | 120 |
| gtattggtgt | ctgaacatca | tttctccaaa | aatggcatta | tagggagcc | cttaaccgct | 180 |
| atatctttcc | ttttaggtct | aaccaagaga | atagaaatag | gttctttgaa | tcaggttata | 240 |
| acgacccacc | atcctgtaag | aattggcgaa | cagactggat | tattagatca | gatgtcttac | 300 |
| ggtcgtttcg | ttttaggttt | atcagattgc | gttaatgatt | tcgaaatgga | ttttttttaaa | 360 |
| cgaaaacgta | gttcacaaca | acaacaattc | gaagcatgtt | atgaaatttt | aaatgaagcc | 420 |
| ttaactacga | attattgcca | agcggatgat | gattttttca | attttccgag | gatcagtgta | 480 |
| aatccccatt | gtatctctga | ggttaaacaa | tacatttttgg | catcttctat | gggtgtagtt | 540 |
| gaatgggccg | ctcgaaaagg | tcttcctttta | acgtatagat | ggagtgatag | tttagcagaa | 600 |
| aaagagaagt | attatcagcg | ttacttagcg | gttgctaaag | agaacaatat | agatgtttca | 660 |

| aatatcgatc atcaatttcc tcttcttgta aatattaacg aaaatcgaag aatagcacga | 720 |
| gatgaagtac gtgagtacat tcagagttat gtatcagaag cctatcccac tgaccctaat | 780 |
| attgaacttc gtgtagaaga attgatcgaa caacacgcag tcgggaaagt cgatgaatat | 840 |
| tatgattcta cgatgcacgc tgtcaaagtt actggttcta aaaatttatt attatctttt | 900 |
| gaatctatga aaataaaga tgacgtcact aaacttatca acatgttcaa ccaaaaaatc | 960 |
| aaggataact taataaagtg a | 981 |

```
<210> SEQ ID NO 3
<211> LENGTH: 1437
<212> TYPE: DNA
<213> ORGANISM: Artificial Sequence
<220> FEATURE:
<223> OTHER INFORMATION: Artificial Lux C nucleotide sequence

<400> SEQUENCE: 3
```

| atgatcaaaa aaatccctat gataattggg ggagtagtcc agaacacatc cggttatgga | 60 |
| atgagagaat taacattaaa caataataaa gttaacattc caattatcac acaaagtgat | 120 |
| gtagaagcta ttcaatctct aaatattgag aacaaattga caataaatca gattgtaaat | 180 |
| ttcctttata ctgtaggcca aaaatggaaa tctgagacgt atagtcgtcg attaacttat | 240 |
| atcagagatt taatcaaatt cttaggttat agtcaggaaa tggctaaatt ggaagctaat | 300 |
| tggattagta tgatattatg ttctaaaagt gctttatatg acatagtaga aaatgattta | 360 |
| agtagtcgtc atatcattga tgaatggatt ccccaaggtg aatgctatgt aaaagcattg | 420 |
| cctaagggta agtccgtaca cttgttagca ggaaatgttc ctttatcagg agtaacctcc | 480 |
| atactaagag caattcttac aaaaaatgaa tgcattatta aaactagttc agcagaccca | 540 |
| tttactgcca ctgcacttgt taactctttt atagacgttg atgccgaaca tcctataaca | 600 |
| cgatccatta gtgtaatgta ttggtcccat tctgaagatt tagcaattcc caaacaaata | 660 |
| atgtcttgtg ctgacgttgt tatagcatgg ggaggggacg atgcaataaa atgggcaact | 720 |
| gaacatgcac cttctcacgc agacatattg aaattcggac cgaaaaaatc catttccatt | 780 |
| gtcgataatc tacggatat taaggcagct gctatcggag tggctcatga catttgtttt | 840 |
| tatgatcagc aagcatgctt ctcaacccaa gatatatatt atatcggaga ttcaattgat | 900 |
| attttctttg atgaattagc tcaacagtta aataaatata agacattttt acctaaaggg | 960 |
| gaacgaaatt tcgatgagaa ggcagctttc tcccttactg aaagagagtg tcttttcgca | 1020 |
| aaatataaag ttcaaaaagg tgaatcccaa tcttggttgc ttacccaaag tccagcggga | 1080 |
| agttttggaa atcaaccttt gagtcgttct gcgtatattc atcaggtaaa tgatataagt | 1140 |
| gaagtaatac ccttcgtaca taaggagtt actcaaactg tagctatcgc gccttgggaa | 1200 |
| tcaagtttta aatacagaga tattttggct gagcatggtg ctgagcgtat cattgaagca | 1260 |
| ggaatgaata acatttttcg tgtaggaggt gcccacgatg ggatgcgacc cttgcaacgt | 1320 |
| ttggttaatt atatttctca tgaacgtcct agtacatata caacaaaaga tgttagtgta | 1380 |
| aaaatagaac agacaaggta tcttgaagaa gataaattct tagttttgt accgtag | 1437 |

```
<210> SEQ ID NO 4
<211> LENGTH: 948
<212> TYPE: DNA
<213> ORGANISM: Artificial Sequence
<220> FEATURE:
<223> OTHER INFORMATION: Artificial Lux D nucleotide sequence
```

```
<400> SEQUENCE: 4
atggaaaata cacaacatag tttacctatt gatcacgtaa tcgacatagg tgacaaccgt      60
tacatcaggg tgtgggaaac taaacctaaa acaaagaaa ctaaagaaa taataccata       120 gtgatagcgt ccggttttgc aagaagaatg gatcactttg ctggattagc tgaatatctt    180
gccaacaatg gattccgagt tattagatac gattcactaa atcatgtggg cttgtctagt    240
ggtgaaatta acagtttag tatgtctgta ggtaaacatt ctttgctaac ggtaattgat     300
tggcttaaag aacgaaatat caacaatatt ggactaattg caagttcctt aagtgcccgt    360
atagcctatg aagtagccgc agaaattgat ttatccttcc ttataacagc agttggggtt    420
gtgaatttac gttctactct tgaaaaagca cttaaatatg attatttgca gatggaagtc    480
aatacgattc ctgaagactt aatatttgaa gggcataatc taggttcaaa agttttgtg     540 actgattgtt ttgaaaacaa ctgggattct ttagactcaa ctattaataa aatttgtgag    600
cttgatattc cgttcatagc tttcacttct gatggggatg attgggtttg tcaacatgaa    660
gtaaaacacc tagtgtccaa tgtaaaatct gacaaaaaaa agatatactc tttagttggt    720
agttcccatg atttggggga aaatttggtc gttttacgaa atttctatca aagtatgact    780
aaagctgctg tctcattgga taggcaattg gttgaattag ttgatgaaat catagaacca    840
aattttgagg atttaaccgt aattacagtc aatgaaagaa gacttaaaaa taaaatagaa    900
aatgaaataa taaacagact agcagatcga gttcttgctt ccgtataa                948

<210> SEQ ID NO 5
<211> LENGTH: 1122
<212> TYPE: DNA
<213> ORGANISM: Artificial Sequence
<220> FEATURE:
<223> OTHER INFORMATION: Artificial Lux E nucleotide sequence

<400> SEQUENCE: 5
atgtccacct tactaaacat cgatgcaacg gagattaaag ttagtaccga gatagatgat     60
ataatcttta caagtagtcc attaacttta ttatttgaag atcaagaaaa aattcagaaa    120
gaattaatac ttgaaagttt tcattatcat tataaccata ataagattc caagtattat     180 tgtaatattc aggggggttga tgagaacatt caatcaattg acgacattcc agtatttcct    240
acatccatgt ttaaatactc tcgtcttcat acagccgatg agtaatat agaaaattgg       300 tttacatcat ccggtactaa aggcgttaag tctcatattg ctagggatag gcagtcaatt    360
gaaagattac taggatcagt taattatggt atgaaatatc ttggagaatt tcatgaacat    420
caacttgaac ttgtaaatat gggaccagat cgttttttccg cttcaaacgt gtggttcaaa    480
tatgttatga gttagtagaa attgttatat cctactactt ttactgtgga aaatgatgag    540
atagattttg aacaaactat cttggcttta aaagcgatac aacgaaaagg aaaaggaata    600
tgtttaatag gaccgcctta ttttatatac ttgttatgcc attatatgaa agaacataat    660
atagaattta atgcaggggc tcacatgttt attattacgg gaggggatg gaaaacaaaa    720 caaaaagagg cgttaaatag gcaagatttc aatcaacttc ttatggaaac attctcctta    780
tttcatgagt cacaaattag agacatattt aatcaagttg aattgaatac atgtttcttc    840
gaagattctc ttcaacgaaa acatgtgcca ccttgggtat atgctcgtgc attagatcct    900
gttactttga ctcccgtaga agacgggcag gaaggcttga tgtcttatat ggacgcctcc    960
agtacatcat atccgacttt catcgttacg gatgatattg gcattgtaag gcatctaaaa    1020
gagccagatc ccttccaagg tacaaccgta gaaattgtta gacgtcttaa cacacgagag    1080
```
caaaagggtt gttctttatc tatggctaca agtcttaaat aa        1122

<210> SEQ ID NO 6
<211> LENGTH: 705
<212> TYPE: DNA
<213> ORGANISM: Artificial Sequence
<220> FEATURE:
<223> OTHER INFORMATION: Artificial Lux G nucleotide sequence

<400> SEQUENCE: 6
atgatcttca actgtaaagt caaaaaagtt gaagcatccg attcacatat ttataaagtc        60
tttatcaaac ccgataagtg tttcgatttt aaagcaggcc aatatgttat tgtgtaccta       120
aacgggaaaa atttaccatt tagtatagcc aactgtccta catgtaatga attattggaa       180
ttacatgtag gcgggtctgt aaaagaatct gcaattgaag caatatcaca ctttattaat       240
gcttttatat atcaaaaaga atttactatt gatgctccgc atggagacgc tggttacga        300
gatgagtctc aatctccgct tttgttaata gctggcggca caggtttatc atatatcaat       360
agtattttaa gttgctgcat tctaaacaa ctatcccaac cgatctattt atactggggt        420
gtcaacaatt gtaaccttt gtatgcagat caacaattaa aaactttggc cgcacaatat        480
cgtaatatta attatatccc tgtagttgag aatcttaata cagattggca aggaaaaatt       540
gggaatgtaa tagatgcagt aatcgaagat tttagtgacc tttcagattt cgacatctat       600
gtttgtggac ccttcggtat gtccagaaca gctaaagata ttctaatttc acaaaagaaa       660
gcaaacatag ggaagatgta ttcagatgct ttttcttaca cgtga                       705

<210> SEQ ID NO 7
<211> LENGTH: 702
<212> TYPE: DNA
<213> ORGANISM: Artificial Sequence
<220> FEATURE:
<223> OTHER INFORMATION: Artificial E.coli Fre nucleotide sequence

<400> SEQUENCE: 7
atgactactc tttcttgtaa ggtgacatca gtggaggcta taactgacac agtgtacaga        60
gttagaatcg taccagatgc agcatttagt tttagggccg gtcaatattt gatggttgta       120
atggacgaga gagataagag accattcagc atggcctcta ctccagatga aaagggtttt       180
atcgaactgc acattggagc atcagagatc aattatacg caaaagcagt catggacagg        240
atcttaaagg accatcagat tgttgttgat attcctcacg gcgaagcatg gcttagggat       300
gatgaggaaa gacctatgat tctcatcgct ggcggaacag ggttctctta cgctaggtct       360
atactcctca ccgccctagc acgtaatcca aatagggata ttaccatta ctggggtggt        420
agagaagagc agcaccttta cgacctttgc gaattggagg cccttagctt aaagcatcct       480
ggtctacaag ttgtgccagt tgtcgaacaa cctgaggcag gatggagagg cgtacagga        540
acagtgctaa ctgccgtttt acaggatcat ggcactcttg ctgagcacga tatttatatt       600
gccggtagat tcgaaatggc taagattgca cgtgaccttt tttgttctga aagaaatgcc       660
agggaagata gattgttcgg tgatgctttc gcattcattt ga                         702

<210> SEQ ID NO 8
<211> LENGTH: 948
<212> TYPE: DNA
<213> ORGANISM: Artificial Sequence
<220> FEATURE:
<223> OTHER INFORMATION: Mutated artificial LuxD nucleotide sequence

<400> SEQUENCE: 8

```
atggaaaata cacaacatag tttacctatt gatcacgtaa tcgacatagg tgacaaccgt    60
tacatcaggg tgtgggaaac taaacctaaa acaaagaaa ctaaagaaa taataccata   120
gtgatagcgt ccggttttgc aagaagaatg gatcactttg ctggattagc tgaatatctt   180
gccaacaatg gattccgagt tattagatac gattcactaa atcatgtggg cttgtctagt   240
ggtgaaatta aacagtttag tatgtctgta ggtaaacatt ctttgctagc ggtaattgat   300
tggcttaaag aacgaaatat caacaatatt ggactaattg caagttcctt aagtgcccgt   360
atagcctatg aagtagccgc agaaattgat ttatccttcc ttataacagc agttggggtt   420
gtgaatttac gttctactct tgaaaagca cttaaatatg attatttgca gatggaagtc   480
aatacgattc ctgaagactt aatatttgaa gggcataatc taggttcaaa agttttgtg   540
actgattgtt ttgaaaacaa ctgggattct ttagactcaa ctattaataa aatttgtgag   600
cttgatattc cgttcatagc tttcacttct gatgggatg attgggtttg tcaacatgaa   660
gtaaaacacc tagtgtccaa tgtaaaatct gacaaaaaa agatatactc tttagttggt   720
agttcccatg atttggggga aaatttggtc gttttacgaa atttctatca agtatgact   780
aaagctgctg tctcattgga taggcaattg gttgaattag ttgatgaaat catagaacca   840
aattttgagg atttaaccgt aattacagtc aatgaaagaa gacttaaaaa taaaatagaa   900
aatgaaataa taaacagact agcagatcga gttcttgctt ccgtataa             948
```

<210> SEQ ID NO 9
<211> LENGTH: 315
<212> TYPE: PRT
<213> ORGANISM: Photobacterium leiognathi

<400> SEQUENCE: 9

```
Met Glu Asn Thr Gln His Ser Leu Pro Ile Asp His Val Ile Asp Ile
1               5                   10                  15

Gly Asp Asn Arg Tyr Ile Arg Val Trp Glu Thr Lys Pro Lys Asn Lys
            20                  25                  30

Glu Thr Lys Arg Asn Asn Thr Ile Val Ile Ala Ser Gly Phe Ala Arg
        35                  40                  45

Arg Met Asp His Phe Ala Gly Leu Ala Glu Tyr Leu Ala Asn Asn Gly
    50                  55                  60

Phe Arg Val Ile Arg Tyr Asp Ser Leu Asn His Val Gly Leu Ser Ser
65                  70                  75                  80

Gly Glu Ile Lys Gln Phe Ser Met Ser Val Gly Lys His Ser Leu Leu
                85                  90                  95

Thr Val Ile Asp Trp Leu Lys Glu Arg Asn Ile Asn Asn Ile Gly Leu
            100                 105                 110

Ile Ala Ser Ser Leu Ser Ala Arg Ile Ala Tyr Glu Val Ala Ala Glu
        115                 120                 125

Ile Asp Leu Ser Phe Leu Ile Thr Ala Val Gly Val Asn Leu Arg
    130                 135                 140

Ser Thr Leu Glu Lys Ala Leu Lys Tyr Asp Tyr Leu Gln Met Glu Val
145                 150                 155                 160

Asn Thr Ile Pro Glu Asp Leu Ile Phe Glu Gly His Asn Leu Gly Ser
                165                 170                 175

Lys Val Phe Val Thr Asp Cys Phe Glu Asn Asn Trp Asp Ser Leu Asp
            180                 185                 190

Ser Thr Ile Asn Lys Ile Cys Glu Leu Asp Ile Pro Phe Ile Ala Phe
```

```
            195                 200                 205
Thr Ser Asp Gly Asp Asp Trp Val Cys Gln His Glu Val Lys His Leu
    210                 215                 220

Val Ser Asn Val Lys Ser Asp Lys Lys Lys Ile Tyr Ser Leu Val Gly
225                 230                 235                 240

Ser Ser His Asp Leu Gly Glu Asn Leu Val Val Leu Arg Asn Phe Tyr
                245                 250                 255

Gln Ser Met Thr Lys Ala Ala Val Ser Leu Asp Arg Gln Leu Val Glu
            260                 265                 270

Leu Val Asp Glu Ile Ile Glu Pro Asn Phe Glu Asp Leu Thr Val Ile
        275                 280                 285

Thr Val Asn Glu Arg Arg Leu Lys Asn Lys Ile Glu Asn Glu Ile Ile
    290                 295                 300

Asn Arg Leu Ala Asp Arg Val Leu Ala Ser Val
305                 310                 315

<210> SEQ ID NO 10
<211> LENGTH: 315
<212> TYPE: PRT
<213> ORGANISM: Photobacterium leiognathi

<400> SEQUENCE: 10

Met Glu Asn Thr Gln His Ser Leu Pro Ile Asp His Val Ile Asp Ile
1               5                   10                  15

Gly Asp Asn Arg Tyr Ile Arg Val Trp Glu Thr Lys Pro Lys Asn Lys
            20                  25                  30

Glu Thr Lys Arg Asn Asn Thr Ile Val Ile Ala Ser Gly Phe Ala Arg
        35                  40                  45

Arg Met Asp His Phe Ala Gly Leu Ala Glu Tyr Leu Ala Asn Asn Gly
    50                  55                  60

Phe Arg Val Ile Arg Tyr Asp Ser Leu Asn His Val Gly Leu Ser Ser
65                  70                  75                  80

Gly Glu Ile Lys Gln Phe Ser Met Ser Val Gly Lys His Ser Leu Leu
                85                  90                  95

Ala Val Ile Asp Trp Leu Lys Glu Arg Asn Ile Asn Asn Ile Gly Leu
            100                 105                 110

Ile Ala Ser Ser Leu Ser Ala Arg Ile Ala Tyr Glu Val Ala Ala Glu
        115                 120                 125

Ile Asp Leu Ser Phe Leu Ile Thr Ala Val Gly Val Val Asn Leu Arg
    130                 135                 140

Ser Thr Leu Glu Lys Ala Leu Lys Tyr Asp Tyr Leu Gln Met Glu Val
145                 150                 155                 160

Asn Thr Ile Pro Glu Asp Leu Ile Phe Glu Gly His Asn Leu Gly Ser
                165                 170                 175

Lys Val Phe Val Thr Asp Cys Phe Glu Asn Asn Trp Asp Ser Leu Asp
            180                 185                 190

Ser Thr Ile Asn Lys Ile Cys Glu Leu Asp Ile Pro Phe Ile Ala Phe
        195                 200                 205

Thr Ser Asp Gly Asp Asp Trp Val Cys Gln His Glu Val Lys His Leu
    210                 215                 220

Val Ser Asn Val Lys Ser Asp Lys Lys Lys Ile Tyr Ser Leu Val Gly
225                 230                 235                 240

Ser Ser His Asp Leu Gly Glu Asn Leu Val Val Leu Arg Asn Phe Tyr
                245                 250                 255
```

```
Gln Ser Met Thr Lys Ala Ala Val Ser Leu Asp Arg Gln Leu Val Glu
            260                 265                 270

Leu Val Asp Glu Ile Ile Glu Pro Asn Phe Glu Asp Leu Thr Val Ile
        275                 280                 285

Thr Val Asn Glu Arg Arg Leu Lys Asn Lys Ile Glu Asn Glu Ile Ile
    290                 295                 300

Asn Arg Leu Ala Asp Arg Val Leu Ala Ser Val
305                 310                 315

<210> SEQ ID NO 11
<211> LENGTH: 585
<212> TYPE: DNA
<213> ORGANISM: Artificial Sequence
<220> FEATURE:
<223> OTHER INFORMATION: Artificial Vibrio fischeri Yellow Fluorescent
      Protein nucleotide sequence

<400> SEQUENCE: 11
atgtttaaag gaattgtgga aggcattgga atcattgaga agatagacat atatacagac      60
cttgacaagt atgccatcag attccctgaa aacatgttga acggcattaa aaaagagtct    120
tccattatgt ttaacggctg ctttcttaca gtgaccagcg ttaatagcaa catcgtctgg    180
tttgatattt ttgagaagga agctaggaaa ctggatacat ttagagaata taaggttgga    240
gatagagtca atttgggtac attcccaaag tttggtgctg catctggagg acatattttg    300
agtgcaagaa tatcttgcgt tgctagtatt attgagatta tagagaatga agattatcaa    360
cagatgtgga ttcagattcc tgagaacttt actgagttct taattgacaa agactatatt    420
gctgtcgatg gtatctcttt aacaatcgac actataaaaa acaatcagtt ttttattagt    480
ttgccgttaa aaatagctca aaataccaac atgaaatgga ggaaaaaggg agataaggtt    540
aacgtggagt tgtctaataa gattaacgct aatcagtgtt ggtga                    585
```